United States Patent
Copt et al.

(10) Patent No.: US 11,284,854 B2
(45) Date of Patent: *Mar. 29, 2022

(54) NOISE REDUCTION ASSEMBLY FOR AUSCULTATION OF A BODY

(71) Applicant: BONGIOVI ACOUSTICS LLC, Port St. Lucie, FL (US)

(72) Inventors: Ryan J. Copt, Port St. Lucie, FL (US); Joseph G. Butera, III, Stuart, FL (US); Robert J. Summers, III, Port St. Lucie, FL (US)

(73) Assignee: BONGIOVI ACOUSTICS LLC, Port St. Lucie, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/088,125

(22) Filed: Nov. 3, 2020

(65) Prior Publication Data

US 2021/0251597 A1    Aug. 19, 2021

Related U.S. Application Data

(63) Continuation of application No. 15/403,598, filed on Jan. 11, 2017, now Pat. No. 10,820,883, which is a
(Continued)

(51) Int. Cl.
 *H04R 1/46*  (2006.01)
 *G10K 11/04*  (2006.01)
(Continued)

(52) U.S. Cl.
CPC ............... *A61B 7/04* (2013.01); *A61B 7/02* (2013.01); *G10K 11/04* (2013.01); *G10K 11/168* (2013.01)

(58) Field of Classification Search
CPC . A61B 7/04; A61B 7/02; G10K 11/04; G10K 11/168; H04R 1/46
(Continued)

(56) References Cited

U.S. PATENT DOCUMENTS

| 2,643,729 A | 6/1953 | McCracken |
| 2,755,336 A | 7/1956 | Zener et al. |

(Continued)

FOREIGN PATENT DOCUMENTS

| AU | 2015247557 | 5/2020 |
| BR | 9611417 | 2/1999 |

(Continued)

OTHER PUBLICATIONS

Stephan Peus et al, Naturliche Horen mit kunstlichern Kopf, Funkschau-Zeitschrift for elektronische Kommunikation; 3i December i 983 (i 983-i 2-3i ), pp. i-4, XP05545i 269; Feb. 14, 2018.
(Continued)

*Primary Examiner* — Ammar T Hamid
(74) *Attorney, Agent, or Firm* — Malloy & Malloy, P.L.

(57) ABSTRACT

The present invention relates to a noise reduction assembly for auscultation of a body. An embodiment of the assembly includes an auscultation device formed of a first material and having a proximal end for engagement with the body when the auscultation device is in an operative orientation. An interior dampening layer, which may be formed of a second material, is formed along an exterior surface of the auscultation device and covering all exterior surfaces thereof except the proximal end. An exterior dampening layer, which may be formed of a third material, is then formed in covering relations relative to the interior dampening layer.

15 Claims, 11 Drawing Sheets

Related U.S. Application Data continuation-in-part of application No. 14/607,513, filed on Jan. 28, 2015, now Pat. No. 10,639,000, which is a continuation-in-part of application No. 14/476,134, filed on Sep. 3, 2014, now Pat. No. 9,615,813.

(60) Provisional application No. 62/313,236, filed on Mar. 25, 2016, provisional application No. 61/980,302, filed on Apr. 16, 2014.

(51) Int. Cl.
*A61B 7/04* (2006.01)
*G10K 11/168* (2006.01)
*A61B 7/02* (2006.01)

(58) Field of Classification Search
USPC .......................................................... 600/586
See application file for complete search history.

(56) References Cited

U.S. PATENT DOCUMENTS

| | | |
|---|---|---|
| 3,396,241 A | 8/1968 | Anderson et al. |
| 3,430,007 A | 2/1969 | Thielen |
| 3,795,876 A | 3/1974 | Takahashi et al. |
| 3,813,687 A | 5/1974 | Geil |
| 4,008,711 A | 2/1977 | Olinger et al. |
| 4,162,462 A | 7/1979 | Endoh et al. |
| 4,184,047 A | 1/1980 | Langford |
| 4,218,950 A | 8/1980 | Uetrecht |
| 4,226,533 A | 10/1980 | Snowman |
| 4,257,325 A | 3/1981 | Bertagni |
| 4,353,035 A | 10/1982 | Schroder |
| 4,356,558 A | 10/1982 | Owen et al. |
| 4,363,007 A | 12/1982 | Haramoto et al. |
| 4,392,027 A | 7/1983 | Bock |
| 4,399,474 A | 8/1983 | Coleman, Jr. |
| 4,412,100 A | 10/1983 | Orban |
| 4,458,362 A | 7/1984 | Berkovitz et al. |
| 4,489,280 A | 12/1984 | Bennett, Jr. et al. |
| 4,517,415 A | 5/1985 | Laurence |
| 4,538,297 A | 8/1985 | Waller, Jr. |
| 4,546,779 A | 10/1985 | Meno |
| 4,549,289 A | 10/1985 | Schwartz et al. |
| 4,584,700 A | 4/1986 | Scholz |
| 4,602,381 A | 7/1986 | Cugnini et al. |
| 4,612,665 A | 9/1986 | Inami et al. |
| 4,641,361 A | 2/1987 | Rosback |
| 4,677,645 A | 6/1987 | Kaniwa et al. |
| 4,696,044 A | 9/1987 | Waller, Jr. |
| 4,701,953 A | 10/1987 | White |
| 4,704,726 A | 11/1987 | Gibson |
| 4,715,559 A | 12/1987 | Fuller |
| 4,739,514 A | 4/1988 | Short et al. |
| 4,815,142 A | 3/1989 | Imreh |
| 4,856,068 A | 8/1989 | Quatieri, Jr. et al. |
| 4,887,299 A | 12/1989 | Cummins et al. |
| 4,997,058 A | 3/1991 | Bertagni |
| 5,007,707 A | 4/1991 | Bertagni |
| 5,073,936 A | 12/1991 | Gorike et al. |
| 5,133,015 A | 7/1992 | Scholz |
| 5,195,141 A | 3/1993 | Jang |
| 5,210,806 A | 5/1993 | Kihara et al. |
| 5,355,417 A | 10/1994 | Burdisso et al. |
| 5,361,381 A | 11/1994 | Short |
| 5,384,856 A | 1/1995 | Kyouno et al. |
| 5,420,929 A | 5/1995 | Geddes et al. |
| 5,425,107 A | 6/1995 | Bertagni et al. |
| 5,463,695 A | 10/1995 | Werrbach |
| 5,465,421 A | 11/1995 | McCormick et al. |
| 5,467,775 A | 11/1995 | Callahan et al. |
| 5,473,214 A | 12/1995 | Hildebrand |
| 5,515,444 A | 5/1996 | Burdisso et al. |
| 5,539,835 A | 7/1996 | Bertagni et al. |
| 5,541,866 A | 7/1996 | Sato et al. |
| 5,572,443 A | 11/1996 | Emoto et al. |
| 5,617,480 A | 4/1997 | Ballard et al. |
| 5,615,275 A | 5/1997 | Bertagni |
| 5,638,456 A | 6/1997 | Conley et al. |
| 5,640,685 A | 6/1997 | Komoda |
| 5,671,287 A | 9/1997 | Gerzon |
| 5,692,059 A | 11/1997 | Kruger |
| 5,693,917 A | 12/1997 | Bertagni et al. |
| 5,699,438 A | 12/1997 | Smith et al. |
| 5,715,821 A | 2/1998 | Faupel |
| 5,727,074 A | 3/1998 | Hildebrand |
| 5,737,432 A | 4/1998 | Werrbach |
| 5,812,684 A | 9/1998 | Mark |
| 5,828,768 A | 10/1998 | Eatwell et al. |
| 5,832,097 A | 11/1998 | Armstrong et al. |
| 5,838,805 A | 11/1998 | Warnaka et al. |
| 5,848,164 A | 12/1998 | Levine |
| 5,861,686 A | 1/1999 | Lee |
| 5,862,461 A | 1/1999 | Yoshizawa et al. |
| 5,872,852 A | 2/1999 | Dougherty |
| 5,883,339 A | 3/1999 | Greenberger |
| 5,901,231 A | 5/1999 | Parrella et al. |
| 5,990,955 A | 11/1999 | Koz |
| 6,002,777 A | 12/1999 | Grasfield et al. |
| 6,053,872 A | 4/2000 | Mohler |
| 6,058,196 A | 5/2000 | Heron |
| 6,078,670 A | 6/2000 | Beyer |
| 6,093,144 A | 7/2000 | Jaeger et al. |
| 6,108,431 A | 8/2000 | Bachler |
| 6,201,873 B1 | 3/2001 | Dal Farra |
| 6,202,601 B1 | 3/2001 | Ouellette et al. |
| 6,208,237 B1 | 3/2001 | Saiki et al. |
| 6,244,376 B1 * | 6/2001 | Granzotto ................ A61B 7/02 |
| | | 181/131 |
| 6,263,354 B1 | 7/2001 | Gandhi |
| 6,285,767 B1 | 9/2001 | Klayman |
| 6,292,511 B1 | 9/2001 | Goldston et al. |
| 6,317,117 B1 | 11/2001 | Goff |
| 6,318,797 B1 | 11/2001 | Bohm et al. |
| 6,332,029 B1 | 12/2001 | Azima et al. |
| 6,343,127 B1 | 1/2002 | Billoud |
| 6,518,852 B1 | 2/2003 | Derrick |
| 6,529,611 B2 | 3/2003 | Kobayashi et al. |
| 6,535,846 B1 | 3/2003 | Shashoua |
| 6,570,993 B1 | 5/2003 | Fukuyama |
| 6,587,564 B1 | 7/2003 | Cusson |
| 6,618,487 B1 | 9/2003 | Azima et al. |
| 6,661,897 B2 | 12/2003 | Smith |
| 6,661,900 B1 | 12/2003 | Allred et al. |
| 6,772,114 B1 | 8/2004 | Sluijter et al. |
| 6,839,438 B1 | 1/2005 | Riegelsberger et al. |
| 6,847,258 B2 | 1/2005 | Ishida et al. |
| 6,871,525 B2 | 3/2005 | Withnall et al. |
| 6,907,391 B2 | 6/2005 | Bellora et al. |
| 6,999,826 B1 | 2/2006 | Zhou et al. |
| 7,006,653 B2 | 2/2006 | Guenther |
| 7,016,746 B2 | 3/2006 | Wiser et al. |
| 7,024,001 B1 | 4/2006 | Nakada |
| 7,058,463 B1 | 6/2006 | Ruha et al. |
| 7,123,728 B2 | 10/2006 | King et al. |
| 7,236,602 B2 | 6/2007 | Gustavsson |
| 7,254,243 B2 | 8/2007 | Bongiovi |
| 7,266,205 B2 | 9/2007 | Miller |
| 7,269,234 B2 | 9/2007 | Klingenbrunn et al. |
| 7,274,795 B2 | 9/2007 | Bongiovi |
| 7,519,189 B2 | 4/2009 | Bongiovi |
| 7,577,263 B2 | 8/2009 | Ourwe |
| 7,613,314 B2 | 11/2009 | Camp, Jr. |
| 7,676,048 B2 | 3/2010 | Tsutsui |
| 7,711,129 B2 | 5/2010 | Lindahl et al. |
| 7,711,442 B2 | 5/2010 | Ryle et al. |
| 7,747,447 B2 | 6/2010 | Christensen et al. |
| 7,764,802 B2 | 7/2010 | Oliver |
| 7,778,718 B2 | 8/2010 | Janke et al. |
| 7,916,876 B1 | 3/2011 | Hetsloot et al. |
| 8,068,621 B2 | 11/2011 | Okabayashi et al. |
| 8,144,902 B2 | 3/2012 | Johnston |
| 8,160,274 B2 | 4/2012 | Bongiovi |

(56) References Cited

U.S. PATENT DOCUMENTS

| | | |
|---|---|---|
| 8,175,287 B2 | 5/2012 | Ueno et al. |
| 8,218,789 B2 | 7/2012 | Bharitkar et al. |
| 8,229,136 B2 | 7/2012 | Bongiovi et al. |
| 8,284,955 B2 | 10/2012 | Bonglovi et al. |
| 8,385,864 B2 | 2/2013 | Dickson et al. |
| 8,462,963 B2 | 6/2013 | Bongiov et al. |
| 8,472,642 B2 | 6/2013 | Bongiov |
| 8,503,701 B2 | 8/2013 | Miles et al. |
| 8,565,449 B2 | 10/2013 | Bongiovi |
| 8,577,676 B2 | 11/2013 | Muesch |
| 8,619,998 B2 | 12/2013 | Walsh et al. |
| 8,705,765 B2 | 4/2014 | Bongiovi |
| 8,750,538 B2 | 6/2014 | Avendano et al. |
| 8,811,630 B2 | 8/2014 | Burlingame |
| 8,879,743 B1 | 11/2014 | Mitra |
| 9,195,433 B2 | 11/2015 | Bongiovi et al. |
| 9,264,004 B2 | 2/2016 | Bongiovi et al. |
| 9,276,542 B2 | 3/2016 | Bongiovi et al. |
| 9,281,794 B1 | 3/2016 | Bongiovi et al. |
| 9,344,828 B2 | 5/2016 | Bongiovi et al. |
| 9,348,904 B2 | 5/2016 | Bongiovi et al. |
| 9,350,309 B2 | 5/2016 | Bongiovi et al. |
| 9,397,629 B2 | 7/2016 | Bongiovi et al. |
| 9,398,394 B2 | 7/2016 | Bongiovi et al. |
| 9,413,321 B2 | 8/2016 | Bongiovi et al. |
| 9,564,146 B2 | 2/2017 | Bongiov et al. |
| 9,615,189 B2 | 4/2017 | Copt et al. |
| 9,621,994 B1 | 4/2017 | Bongiovi et al. |
| 9,638,672 B2 | 5/2017 | Butera, III |
| 9,741,355 B2 | 8/2017 | Bongiovi et al. |
| 9,793,872 B2 | 10/2017 | Bongiovi et al. |
| 9,883,318 B2 | 1/2018 | Bongiovi et al. |
| 9,906,858 B2 | 2/2018 | Bongiovi et al. |
| 9,906,867 B2 | 2/2018 | Bongiovi et al. |
| 9,998,832 B2 | 6/2018 | Bongiovi et al. |
| 10,069,471 B2 | 9/2018 | Bongiovi et al. |
| 10,158,337 B2 | 12/2018 | Bongiovi et al. |
| 10,820,883 B2 * | 11/2020 | Copt ............... A61B 7/04 |
| 2001/0008535 A1 | 7/2001 | Lanigan |
| 2001/0043704 A1 | 11/2001 | Schwartz |
| 2001/0046304 A1 | 11/2001 | Rast |
| 2002/0057808 A1 | 5/2002 | Goldstein |
| 2002/0071481 A1 | 6/2002 | Goodings |
| 2002/0094096 A1 | 7/2002 | Paritsky et al. |
| 2003/0016838 A1 | 1/2003 | Paritsky et al. |
| 2003/0023429 A1 | 1/2003 | Claesson |
| 2003/0035555 A1 | 2/2003 | King et al. |
| 2003/0043940 A1 | 3/2003 | Janky et al. |
| 2003/0112088 A1 | 6/2003 | Bizjak |
| 2003/0138117 A1 | 7/2003 | Goff |
| 2003/0142841 A1 | 7/2003 | Wiegand |
| 2003/0164546 A1 | 9/2003 | Giger |
| 2003/0179891 A1 | 9/2003 | Rabinowitz |
| 2003/0216907 A1 | 11/2003 | Thomas |
| 2004/0003805 A1 | 1/2004 | Ono et al. |
| 2004/0005063 A1 | 1/2004 | Klayman |
| 2004/0008851 A1 | 1/2004 | Hagiwara |
| 2004/0022400 A1 | 2/2004 | Magrath |
| 2004/0044804 A1 | 3/2004 | Mac Farlane |
| 2004/0086144 A1 | 5/2004 | Kallen |
| 2004/0103588 A1 | 6/2004 | Allaei |
| 2004/0138769 A1 | 7/2004 | Akiho |
| 2004/0146170 A1 | 7/2004 | Zint |
| 2004/0189264 A1 | 9/2004 | Matsuura et al. |
| 2004/0208646 A1 | 10/2004 | Choudhary et al. |
| 2005/0013453 A1 | 1/2005 | Cheung |
| 2005/0090295 A1 | 4/2005 | Ali et al. |
| 2005/0117771 A1 | 6/2005 | Vosburgh et al. |
| 2005/0129248 A1 | 6/2005 | Kraemer et al. |
| 2005/0175185 A1 | 8/2005 | Komer |
| 2005/0201572 A1 | 9/2005 | Lindahl et al. |
| 2005/0249272 A1 | 11/2005 | Kirkeby et al. |
| 2005/0254564 A1 | 11/2005 | Tsutsui |
| 2006/0034467 A1 | 2/2006 | Sleboda et al. |
| 2006/0045294 A1 | 3/2006 | Smyth |
| 2006/0064301 A1 | 3/2006 | Aguilar et al. |
| 2006/0098827 A1 | 5/2006 | Paddock et al. |
| 2006/0115107 A1 | 6/2006 | Vincent et al. |
| 2006/0126851 A1 | 6/2006 | Yuen et al. |
| 2006/0126865 A1 | 6/2006 | Blamey et al. |
| 2006/0138285 A1 | 6/2006 | Oleski et al. |
| 2006/0140319 A1 | 6/2006 | Eldredge et al. |
| 2006/0153281 A1 | 7/2006 | Karlsson |
| 2006/0189841 A1 | 8/2006 | Pluvinage |
| 2006/0291670 A1 | 12/2006 | King et al. |
| 2007/0010132 A1 | 1/2007 | Nelson et al. |
| 2007/0030994 A1 | 2/2007 | Ando et al. |
| 2007/0106179 A1 | 5/2007 | Bagha et al. |
| 2007/0119421 A1 | 5/2007 | Lewis et al. |
| 2007/0150267 A1 | 6/2007 | Honma et al. |
| 2007/0173990 A1 | 7/2007 | Smith et al. |
| 2007/0177459 A1 | 8/2007 | Behn et al. |
| 2007/0206643 A1 | 9/2007 | Egan et al. |
| 2007/0223713 A1 | 9/2007 | Gunness |
| 2007/0223717 A1 | 9/2007 | Boersma |
| 2007/0253577 A1 | 11/2007 | Yen et al. |
| 2008/0001735 A1 | 1/2008 | Tran |
| 2008/0031462 A1 | 2/2008 | Walsh et al. |
| 2008/0040116 A1 | 2/2008 | Cronin et al. |
| 2008/0049948 A1 | 2/2008 | Christoph et al. |
| 2008/0069385 A1 | 3/2008 | Revit |
| 2008/0123870 A1 | 5/2008 | Stark et al. |
| 2008/0123873 A1 | 5/2008 | Bjor-Josefsen et al. |
| 2008/0146890 A1 | 6/2008 | LeBoeuf et al. |
| 2008/0165989 A1 | 7/2008 | Seil et al. |
| 2008/0172072 A1 | 7/2008 | Pool et al. |
| 2008/0181424 A1 | 7/2008 | Schulein et al. |
| 2008/0212798 A1 | 9/2008 | Zartarian |
| 2008/0255855 A1 | 10/2008 | Lee et al. |
| 2008/0264180 A1 | 10/2008 | Gakhar |
| 2008/0306373 A1 | 12/2008 | Kandori et al. |
| 2009/0022328 A1 | 1/2009 | Neugebauer et al. |
| 2009/0054109 A1 | 2/2009 | Hunt |
| 2009/0080675 A1 | 3/2009 | Smirnov et al. |
| 2009/0086996 A1 | 4/2009 | Bongiovi et al. |
| 2009/0116652 A1 | 5/2009 | Kirkeby et al. |
| 2009/0211838 A1 | 8/2009 | Bilan |
| 2009/0282810 A1 | 11/2009 | Leone et al. |
| 2009/0290725 A1 | 11/2009 | Huang |
| 2009/0296959 A1 | 12/2009 | Bongiovi |
| 2010/0045374 A1 | 2/2010 | Wu et al. |
| 2010/0246832 A1 | 9/2010 | Villemoes et al. |
| 2010/0256843 A1 | 10/2010 | Bergstein et al. |
| 2010/0278364 A1 | 11/2010 | Berg |
| 2010/0303278 A1 | 12/2010 | Sahyoun |
| 2011/0002467 A1 | 1/2011 | Nielsen |
| 2011/0013736 A1 | 1/2011 | Tsukamoto et al. |
| 2011/0065408 A1 | 3/2011 | Keninglon et al. |
| 2011/0087348 A1 | 4/2011 | Larsen et al. |
| 2011/0096936 A1 * | 4/2011 | Gass ............... A61B 7/04 381/67 |
| 2011/0125063 A1 | 5/2011 | Shalon et al. |
| 2011/0160815 A1 | 6/2011 | Matsumura |
| 2011/0194712 A1 | 8/2011 | Potard |
| 2011/0230137 A1 | 9/2011 | Hicks et al. |
| 2011/0257833 A1 | 10/2011 | Trush et al. |
| 2011/0280411 A1 | 11/2011 | Cheah et al. |
| 2012/0008798 A1 | 1/2012 | Ong |
| 2012/0014553 A1 | 1/2012 | Bonanno |
| 2012/0063611 A1 | 3/2012 | Kimura |
| 2012/0089045 A1 | 4/2012 | Seidl et al. |
| 2012/0099741 A1 | 4/2012 | Gotoh et al. |
| 2012/0170795 A1 | 7/2012 | Sancisi et al. |
| 2012/0189131 A1 | 7/2012 | Ueno et al. |
| 2012/0213034 A1 | 8/2012 | Imran |
| 2012/0213375 A1 | 8/2012 | Mahabub et al. |
| 2012/0300949 A1 | 11/2012 | Rauhala |
| 2012/0302920 A1 | 11/2012 | Bridger et al. |
| 2012/0310216 A1 | 12/2012 | Koltchine et al. |
| 2013/0083958 A1 | 4/2013 | Katz et al. |
| 2013/0129106 A1 | 5/2013 | Sapiejewski |
| 2013/0131519 A1 | 5/2013 | LeBoeuf et al. |
| 2013/0162908 A1 | 6/2013 | Son et al. |
| 2013/0163783 A1 | 6/2013 | Burlingame |

(56) References Cited

U.S. PATENT DOCUMENTS

| | | |
|---|---|---|
| 2013/0169779 A1 | 7/2013 | Pedersen |
| 2013/0220274 A1 | 8/2013 | Deshpande et al. |
| 2013/0227631 A1 | 8/2013 | Sharma et al. |
| 2013/0242191 A1 | 9/2013 | Leyendecker et al. |
| 2013/0251175 A1 | 9/2013 | Bongiov et al. |
| 2013/0288596 A1 | 10/2013 | Suzuki et al. |
| 2013/0338504 A1 | 12/2013 | Demos et al. |
| 2014/0067236 A1 | 3/2014 | Henry et al. |
| 2014/0119583 A1 | 5/2014 | Valentine et al. |
| 2014/0126734 A1 | 5/2014 | Gauger, Jr. et al. |
| 2014/0261301 A1 | 9/2014 | Leone |
| 2014/0379355 A1 | 12/2014 | Hosokawsa |
| 2015/0194158 A1 | 7/2015 | Oh et al. |
| 2015/0208163 A1 | 7/2015 | Hallberg et al. |
| 2015/0215720 A1 | 7/2015 | Carroll |
| 2015/0297170 A1 | 10/2015 | Copt et al. |
| 2016/0133203 A1 | 5/2016 | Jurewicz et al. |
| 2016/0166203 A1 | 6/2016 | Goldstein |
| 2016/0324478 A1 | 11/2016 | Goldstein |
| 2017/0188989 A1 | 7/2017 | Copt et al. |
| 2017/0193980 A1 | 7/2017 | Bongiovi et al. |
| 2017/0272887 A1 | 9/2017 | Copt et al. |
| 2017/0345408 A1 | 11/2017 | Hong et al. |
| 2018/0091109 A1 | 3/2018 | Bongiovi et al. |
| 2018/0102133 A1 | 4/2018 | Bongiovi et al. |
| 2018/0139565 A1 | 5/2018 | Norris et al. |
| 2019/0020950 A1 | 1/2019 | Bongiovi et al. |
| 2019/0318719 A1 | 10/2019 | Copt et al. |
| 2020/0029886 A1 | 1/2020 | Butera, III et al. |
| 2021/0251597 A1 | 8/2021 | Copt et al. |

FOREIGN PATENT DOCUMENTS

| | | |
|---|---|---|
| BR | 96113723 | 7/1999 |
| CA | 2533221 | 6/1995 |
| CA | 2161412 | 4/2000 |
| CA | 2854086 | 12/2018 |
| CN | 1139842 | 1/1997 |
| CN | 11 73268 | 2/1998 |
| CN | 1221528 | 6/1999 |
| CN | 1357136 | 7/2002 |
| CN | 1391780 | 1/2003 |
| CN | 1679372 | 10/2005 |
| CN | 1879449 | 12/2006 |
| CN | 1910816 | 2/2007 |
| CN | 101163354 | 4/2008 |
| CN | 101277331 | 10/2008 |
| CN | 101518083 | 8/2009 |
| CN | 101536541 | 9/2009 |
| CN | 101720557 | 6/2010 |
| CN | 101946526 | 1/2011 |
| CN | 101964189 | 2/2011 |
| CN | 102265641 | 11/2011 |
| CN | 102652337 | 8/2012 |
| CN | 102754151 | 10/2012 |
| CN | 102772222 | 11/2012 |
| CN | 102822891 | 12/2012 |
| CN | 102855882 | 1/2013 |
| CN | 103004237 | 3/2013 |
| CN | 203057339 | 7/2013 |
| CN | 103247297 | 8/2013 |
| CN | 103250209 | 8/2013 |
| CN | 103262577 | 8/2013 |
| CN | 103348697 | 10/2013 |
| CN | 103417240 | 12/2013 |
| CN | 103455824 | 12/2013 |
| CN | 111295139 | 6/2020 |
| DE | 19826171 | 10/1999 |
| DE | 10116166 | 10/2002 |
| EP | 0206746 | 8/1992 |
| EP | 0541646 | 1/1995 |
| EP | 0580579 | 6/1998 |
| EP | 0698298 | 2/2000 |
| EP | 0932523 | 6/2000 |
| EP | 0666012 | 11/2002 |
| EP | 2509069 | 10/2012 |
| EP | 2814267 | 2/2016 |
| ES | 2218599 | 10/1998 |
| ES | 2249788 | 10/1998 |
| ES | 2219949 | 8/1999 |
| GB | 2003707 | 3/1979 |
| GB | 2320393 | 6/1998 |
| HK | 40001907 | 3/2020 |
| JP | 3150910 | 6/1991 |
| JP | 7106876 | 4/1995 |
| JP | 2005500768 | 1/2005 |
| JP | 2011059714 | 3/2011 |
| JP | 2012090909 | 5/2012 |
| JP | 6726169 | 7/2020 |
| JP | 2020533060 | 11/2020 |
| KR | 1020040022442 | 3/2004 |
| SU | 1319288 | 6/1987 |
| TW | 401713 | 8/2000 |
| TW | 201404185 | 1/2014 |
| WO | WO9219080 | 10/1992 |
| WO | WO1993011637 | 6/1993 |
| WO | WO9321743 | 10/1993 |
| WO | WO9427331 | 11/1994 |
| WO | WO9514296 | 5/1995 |
| WO | WO9531805 | 11/1995 |
| WO | WO9535628 | 12/1995 |
| WO | WO9601547 | 1/1996 |
| WO | WO9611465 | 4/1996 |
| WO | WO9709698 | 3/1997 |
| WO | WO9709840 | 3/1997 |
| WO | WO9709841 | 3/1997 |
| WO | WO9709842 | 3/1997 |
| WO | WO9709843 | 3/1997 |
| WO | WO9709844 | 3/1997 |
| WO | WO9709845 | 3/1997 |
| WO | WO9709846 | 3/1997 |
| WO | WO9709847 | 3/1997 |
| WO | WO9709848 | 3/1997 |
| WO | WO9709849 | 3/1997 |
| WO | WO9709853 | 3/1997 |
| WO | WO9709854 | 3/1997 |
| WO | WO9709855 | 3/1997 |
| WO | WO9709856 | 3/1997 |
| WO | WO9709857 | 3/1997 |
| WO | WO9709858 | 3/1997 |
| WO | WO9709859 | 3/1997 |
| WO | WO9709861 | 3/1997 |
| WO | WO9709862 | 3/1997 |
| WO | WO9717818 | 5/1997 |
| WO | WO9717820 | 5/1997 |
| WO | WO9813942 | 4/1998 |
| WO | WO9816409 | 4/1998 |
| WO | WO9828942 | 7/1998 |
| WO | WO9831188 | 7/1998 |
| WO | WO9834320 | 8/1998 |
| WO | WO9839947 | 9/1998 |
| WO | WO9842536 | 10/1998 |
| WO | WO9843464 | 10/1998 |
| WO | WO9852381 | 10/1998 |
| WO | WO9852383 | 11/1998 |
| WO | WO9853638 | 11/1998 |
| WO | WO9902012 | 1/1999 |
| WO | WO9908479 | 2/1999 |
| WO | WO9911490 | 3/1999 |
| WO | WO9912387 | 3/1999 |
| WO | WO9913684 | 3/1999 |
| WO | WO9921397 | 4/1999 |
| WO | WO9935636 | 7/1999 |
| WO | WO9935883 | 7/1999 |
| WO | WO9937121 | 7/1999 |
| WO | WO9938155 | 7/1999 |
| WO | WO9941939 | 8/1999 |
| WO | WO9952322 | 10/1999 |
| WO | WO9952324 | 10/1999 |
| WO | WO9956497 | 11/1999 |
| WO | WO9962294 | 12/1999 |
| WO | WO9965274 | 12/1999 |
| WO | WO0001264 | 1/2000 |
| WO | WO0002417 | 1/2000 |

(56) References Cited

FOREIGN PATENT DOCUMENTS

| WO | WO0007408 | 2/2000 |
|---|---|---|
| WO | WO0007409 | 2/2000 |
| WO | WO0013464 | 3/2000 |
| WO | WO0015003 | 3/2000 |
| WO | WO0033612 | 6/2000 |
| WO | WO0033613 | 6/2000 |
| WO | WO2003088841 | 10/2003 |
| WO | WO03104924 | 12/2003 |
| WO | WO2006020427 | 2/2006 |
| WO | WO2007092420 | 8/2007 |
| WO | WO2008067454 | 6/2008 |
| WO | WO2009070797 | 6/2009 |
| WO | WO2009102750 | 8/2009 |
| WO | WO2009114746 | 9/2009 |
| WO | WO2009155057 | 12/2009 |
| WO | WO2010027705 | 3/2010 |
| WO | WO2010051354 | 5/2010 |
| WO | WO2011081965 | 7/2011 |
| WO | WO2012134399 | 10/2012 |
| WO | WO2013055394 | 4/2013 |
| WO | WO2013076223 | 5/2013 |
| WO | WO2013142653 | 9/2013 |
| WO | WO2014201103 | 12/2014 |
| WO | WO2015061393 | 4/2015 |
| WO | WO2015077681 | 5/2015 |
| WO | WO2015161034 | 10/2015 |
| WO | WO2016019263 | 2/2016 |
| WO | WO2016022422 | 2/2016 |
| WO | WO2016144861 | 9/2016 |
| WO | WO2019051075 | 3/2019 |
| WO | WO 2019200119 | 10/2019 |
| WO | WO 2020028796 | 2/2020 |

OTHER PUBLICATIONS

Stephan Peus et al., Natrliche Hren mite knstlichem Kopf, Funkschau Zeitschrift fr elektronische Kommunikation, pp. 1-4, XP055451269. Web: https://www.neumann.com?lang-en&id=hist_microphones&cid=ku80_publications., Dec. 31, 1983.

Novasound Int., http://www.novasoundint.com/new_page_t.htm, 2004, Jan. 1, 2004.

Stephen Peus, Natural Listening With a Dummy Head, Georg Neumann GmbH, Berlin, p. 1-4, Jul. 31, 1985, Jul. 31, 1985.

Benjamin Stein et al., Mechanical and Electrical Equipment for Buildings, Apr. 30, 2003, pp. 1590-1594, Publisher: Dalian University of Technology Press.

* cited by examiner

NOISE REDUCTION ASSEMBLY FOR AUSCULTATION OF A BODY

CLAIM OF PRIORITY

This application is a Continuation-In-Part of U.S. patent Ser. No. 15/403,598 and a filing date of Jan. 11, 2017, which is set to mature into U.S. Pat. No. 10,820,883 on Nov. 3, 2020, which is a continuation-in-part of a currently pending U.S. patent application having Ser. No. 14/607,513 and a filing date of Jan. 28, 2015, which matured into U.S. Pat. No. 10,639,000 on May 5, 2020 and which is a continuation-in-part of pending U.S. patent application having Ser. No. 14/476,134 and a filing date of Sep. 3, 2014, which matured into U.S. Pat. No. 9,615,813 on Apr. 11, 2017 which made a claim of priority to a U.S. Provisional patent application having Ser. No. 61/980,302, filed Apr. 16, 2014.

Additionally, this application is a Continuation-In-Part of U.S. patent Ser. No. 15/403,598 which further claims priority to provisional patent application 62/313,236, filed Mar. 25, 2016.

Each of the above prior-filed applications are hereby incorporated by reference in their entireties.

BACKGROUND OF THE INVENTION

Field of the Invention

The present invention relates to a device for auscultation of a body. An embodiment of the device includes a housing dimensioned and configured for disposition in an operative orientation relative to a predetermined portion of the body, the housing having a plurality of chambers disposed therewithin, the housing also being surrounded by a concentric structure. A further embodiment also comprises one or more noise impeding materials disposed within the chamber(s) for reducing ambient noise leakage into the auscultation device of the present invention.

Description of the Related Art

Auscultation, or the term for listening to the internal sounds of a body, is of great importance to many disciplines, such as the medical fields. For example, auscultation of a body, such as the body of a patient, assists a medical professional in the diagnosis of ailments that may affect the patient. Such may be traditionally achieved with a stethoscope, which may use a wide bell and/or a diaphragm to listen to a narrow range of low frequency acoustic signals, such as those associated with patient's heartbeat. However, such approaches are fundamentally inadequate for many other diagnostic purposes, such as receiving acoustic signals associated with higher frequency signals.

Accordingly, what is needed in the art is a device structured to receive acoustic signals in a wider band of frequencies, including but not limited to high-frequency sounds. Such acoustic signals include frequencies associated with other functions of the body useful in diagnosis, such as swallowing, breathing, and blood flow, and are outside the capabilities of traditional stethoscope devices.

Further, what is needed in the art is a system incorporating such a device. Such a system may incorporate the device to facilitate in the diagnosis of patients and/or other medical procedures carried out by medical professionals. Such a system would utilize the acoustic signals received by the device, and process the signals to assist in detection of, for example, disorders of the gut, the joints, the lungs, blood flow, or swallowing.

SUMMARY OF THE INVENTION

The present invention relates to a device for auscultation of a body, such as the body of a patient. An illustrative embodiment of a device in accordance with the present invention comprises a housing dimensioned and configured for disposition in an operative orientation relative to a predetermined portion of the body. Examples of such predetermined portion of the body include but are not limited to the throat and area corresponding to the lungs.

Included within the housing are a plurality of chambers collectively structured to receive an acoustic signal at least when the housing is disposed in the operative orientation. The acoustic signals are produced by the body and may correlate with various bodily processes, conditions, etc. Receiving such signals may facilitate diagnostics and other medical procedures. Accordingly, the plurality of chambers are cooperatively structured and/or shaped such that acoustic signals produced by the body enter the device for detection.

Additionally, at least partially disposed within one of the plurality of chambers is at least one transducer. The transducer is structured to convert the audio signal received by the device into an electrical signal. By way of example only, the transducer may comprise a microphone. The electrical signal may then be transmitted to other elements of a diagnostic system, as will be further described herein.

A preferred embodiment of the present invention further comprises proximal and distal ends, the proximal end being structured to define an opening. The opening is dimensioned and configured for engagement with the predetermined portion of the body.

Further, the plurality of chambers comprises an acoustic capture chamber in a sound receiving relationship relative to the opening. Accordingly, the sound receiving relationship permits the passage of the acoustic signal from the opening to at least the acoustic capture chamber. In the preferred embodiment, this is achieved by way of the opening permitting entry of the acoustic signal into the acoustic capture chamber.

It should be appreciated that the shape of the acoustic capture chamber may vary among the various embodiments of the present invention. However, in a preferred embodiment, the diameter of the distal end of the acoustic capture chamber is less than or equal to the diameter of a proximal end. An example of a geometric shape having such a configuration wherein one end comprises a smaller diameter than an opposing end is a frustum of a right circular cone. Accordingly, various embodiments of an acoustic capture chamber may comprise such a configuration. However, the acoustic chamber may comprise any suitable shape in accordance with the present invention, including but not limited to the foregoing.

In addition, the plurality of chambers comprises a primary resonance chamber disposed in sound receiving relation relative to the acoustic capture chamber. In a preferred embodiment, the transducer is at least partially disposed within the primary resonance chamber. In addition, in a preferred embodiment, the transducer is movably disposed in the primary resonance chamber.

Moreover, a preferred embodiment of the primary resonance chamber comprises a resonance adjustment member movably disposed within the primary resonance chamber. Adjustment of the resonance adjustment member, such as by moving it within the primary resonance chamber, facilitates alteration of acoustic properties of the device. Further, in a preferred embodiment such adjustment may be carried out during use of the device.

A preferred embodiment further comprises a secondary resonance chamber disposed in a sound receiving relationship relative to the acoustic capture chamber. The secondary resonance chamber facilitates "tuning" of the device, such as by adjusting a range of acoustic signals that the device receives or to which it is most sensitive. In a preferred embodiment, this is accomplished by altering the physical parameters, such as the volume, of the secondary resonance chamber. Further, in a preferred embodiment, at least one transducer is movably disposed at least partially within the secondary resonance chamber. Accordingly, moving of the transducer facilitates "tuning" of the device, such as by altering the resonant properties of the device.

The present invention further relates to a signal processing system. In a preferred embodiment of the system, at least one device is in communication with a plurality of components collectively configured to process an electrical signal received from the device. The electrical signal corresponds to the acoustic signal received by the device from the body. The plurality of components in the preferred embodiment includes an amplification component, a digital signal processing component, an analysis component, a pattern recognition component, and at least one output component.

Another preferred embodiment of the present invention relates to a device for auscultation of a body to include low frequency signals, including those at or below 500 Hz. Accordingly, the device in this embodiment may comprise a housing as well as a concentric structure.

The housing may comprise a plurality of chambers collectively structured to receive an acoustic signal at least when the housing is disposed in the operative orientation, such as when the proximal end of the housing is placed up against a resonating body such as a patient's body for auscultation. The plurality of chambers may comprise an acoustic capture chamber and a primary resonance chamber, and may further comprise a secondary resonance chamber in some embodiments. A transducer may be disposed at least partially in the primary resonance chamber and/or the secondary resonance chamber. The acoustic capture chamber is disposed in a sound receiving relationship relative to an opening of the housing, and is structured to receive acoustic signals of higher frequencies, such as those at or above 500 Hz.

The concentric structure is formed circumferentially in surrounding relations to the proximal end of the housing. The proximal end of the concentric structure may be flush or parallel with the proximal end of the housing. An exterior of the concentric structure may form a bell shape, such that an opening of the concentric structure along its proximal end extends to a substantially hollow opening therein, while the distal portion may form a substantially flat profile in surrounding and abutting relations with an exterior of the housing.

The housing may further comprise a low frequency receiver, such as a bore formed between an exterior of the housing but within the canopy of the concentric structure that reaches inward to an interior opening of the acoustic capture chamber. This low frequency receiver or bore is structured to receive the lower frequency sounds at the acoustic capture chamber and/or at the primary or secondary resonance chamber(s) housing the transducer. The transducer may then convert both the received higher frequency signals from the opening of the housing, as well as the low frequency signals from the opening of the concentric structure, into an electrical input signal for further processing.

A further embodiment of the present invention comprises layering an interior dampening layer in surrounding and overlying relations relative to an auscultation device on all exterior surfaces except the proximal end placed against the body. A further exterior dampening layer may be further disposed in surrounding and overlying relations relative to the interior dampening layer. Each of the interior dampening layer, exterior dampening layer, and the auscultation device itself or the exterior surface thereof, may be formed of a different material to maximizing the range of extraneous and external noises that is impeded.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As illustrated in the accompanying drawings, the present invention is directed to a device and system for auscultation of a body. As described above, auscultation relates to the practice of capturing acoustic signals produced by the body, such as but not limited to for purposes of medical diagnosis. Accordingly, it should be appreciated that the body may be a human body, i.e. a patient, but may also be any other suitable source of acoustic signals.

Figure 1:
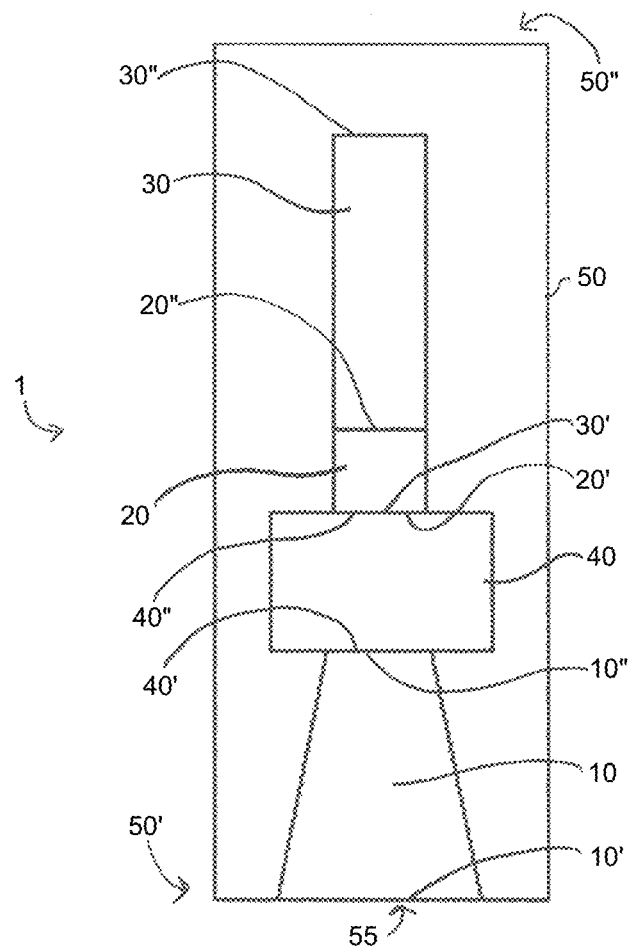
FIG. 1 is a schematic representation of a side view of an illustrative embodiment of a device in accordance with the present invention.

In accordance with the illustrative embodiment as shown in FIG. 1, a device 1 comprises a housing 50. The housing 50 is dimensioned and configured for disposition in an operative orientation relative to a predetermined portion of the body. For example, the housing 50 may be placed relative to and/or against a portion of the body that corresponds to a patient's throat, such as for purposes of monitoring acoustic signals associated with a patient's breathing and/or swallowing.

Accordingly, the housing 50 comprises a plurality of chambers 10, 30, 40 disposed within the housing. The chambers are collectively structured to receive an acoustic signal produced by the body. In a preferred embodiment, the chambers 10, 30, 40 are collectively structured such that receiving the acoustic signal causes the housing 50 to resonate. Further, in a preferred embodiment, chambers 10, 30, 40 are collectively structured such that housing 50 resonates at a frequency and/or frequencies within the range of about 20 Hertz to about 2,000 Hertz. In addition, the housing 50 in a preferred embodiment comprises a material of construction chosen for particular resonant properties.

With further reference to FIG. 1, the housing 50 comprises a proximal end 50' and a distal end 50". The proximal end 50' is structured for disposition in an operative orientation relative to a predetermined portion of the body, such as an area of the neck, throat, an area of the chest, and/or any other desired or suitable area. Such disposition of the proximal end 50' comprises engagement of the housing 50 with the body such that the housing 50 and the body define a confronting engagement with one another.

Further, the proximal end 50' is structured to include an opening 55. The opening 55 is dimensioned and configured for engagement with the predetermined portion of the body when the housing 50 is in the operative orientation. Engagement of the opening 55 with the body includes disposition of the opening 55 in close proximity to the body such that acoustic signals produced by the body pass through the opening 55 and into the housing 50. Accordingly, various embodiments of the present invention may comprise varying configurations and/or dimensions of openings 55 suitable for engagement with varying predetermined portions of the body, as may be determined by e.g. the size and location of the predetermined portion of the body.

The plurality of chambers 10, 30, 40 of the embodiment of FIG. 1 comprise an acoustic capture chamber 10. The acoustic capture chamber 10 is disposed in a sound receiving relationship to the opening 55. Accordingly, the opening 55 facilitates passage of acoustic signals into the acoustic capture chamber 10.

Figure 2:
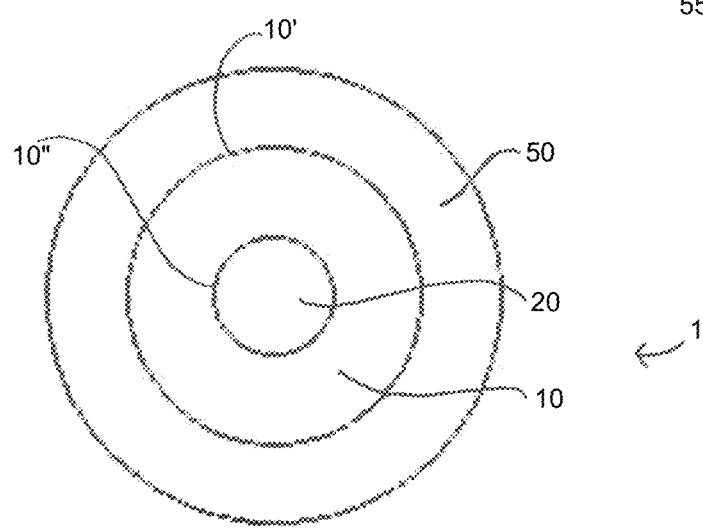
FIG. 2 is a schematic representation of a bottom view of the embodiment of FIG. 1.
Figure 4:
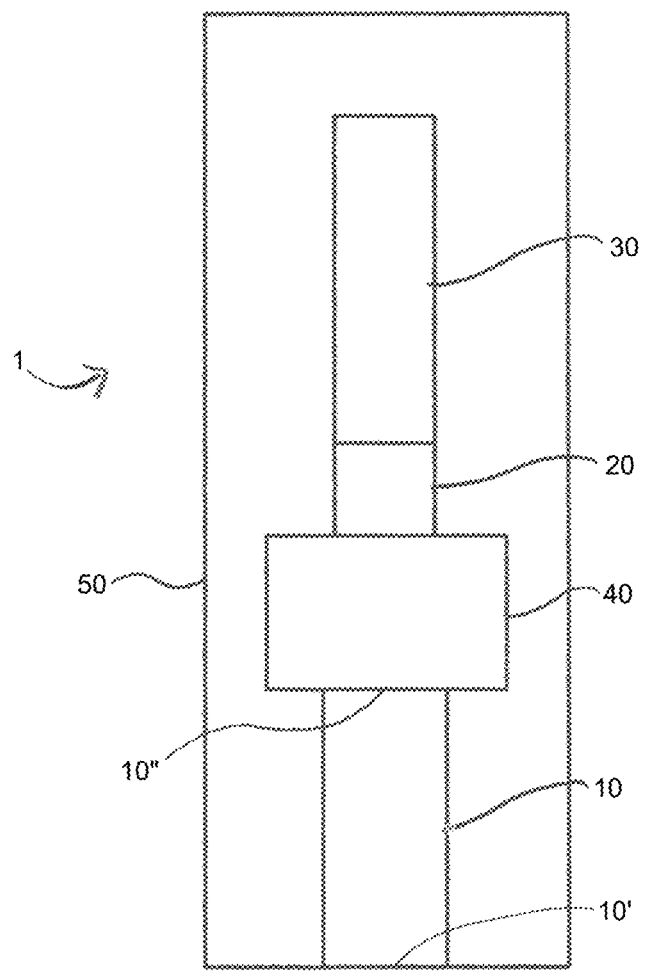
FIG. 4 is a schematic representation of a side view of an illustrative embodiment of a device in accordance with the present invention.

FIG. 2 shows the embodiment of FIG. 1 as seen from a view toward the opening 55. The acoustic capture chamber comprises a proximal end 10' and a distal end 10". Further, various embodiments of an acoustic capture chamber 10 comprising various configurations are contemplated. As is evident from FIG. 2, in a preferred embodiment, the distal end 10" of the acoustic capture chamber 10 comprises a diameter less than a diameter of the proximal end 10'. FIG. 4 illustrates a preferred embodiment wherein the distal end 10" of the acoustic capture chamber 10 comprises a diameter equal to a diameter of the proximal end 10'.

With further reference to FIG. 1, a preferred embodiment of the device 1 comprises a primary resonance chamber 30. The primary resonance chamber 30 is disposed in a sound receiving relationship relative to the acoustic capture chamber 10. Accordingly, acoustic signals produced by the body that are captured and/or received by the acoustic capture chamber 10 are received by the primary resonance chamber 30.

Figure 5:
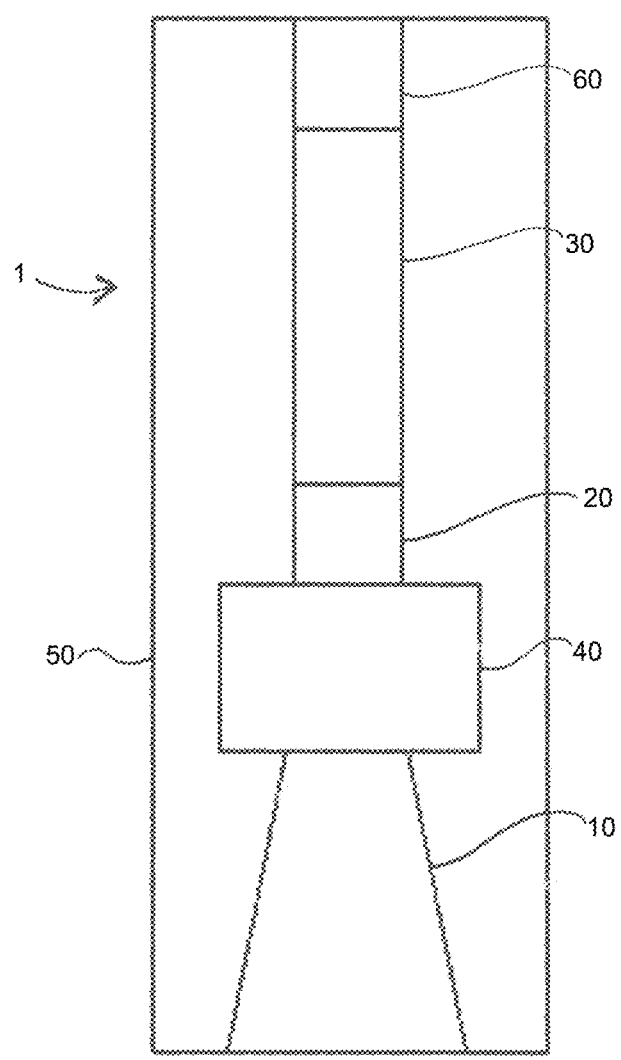
FIG. 5 is a schematic representation of a side view of an illustrative embodiment of a device in accordance with the present invention.
Figure 6:
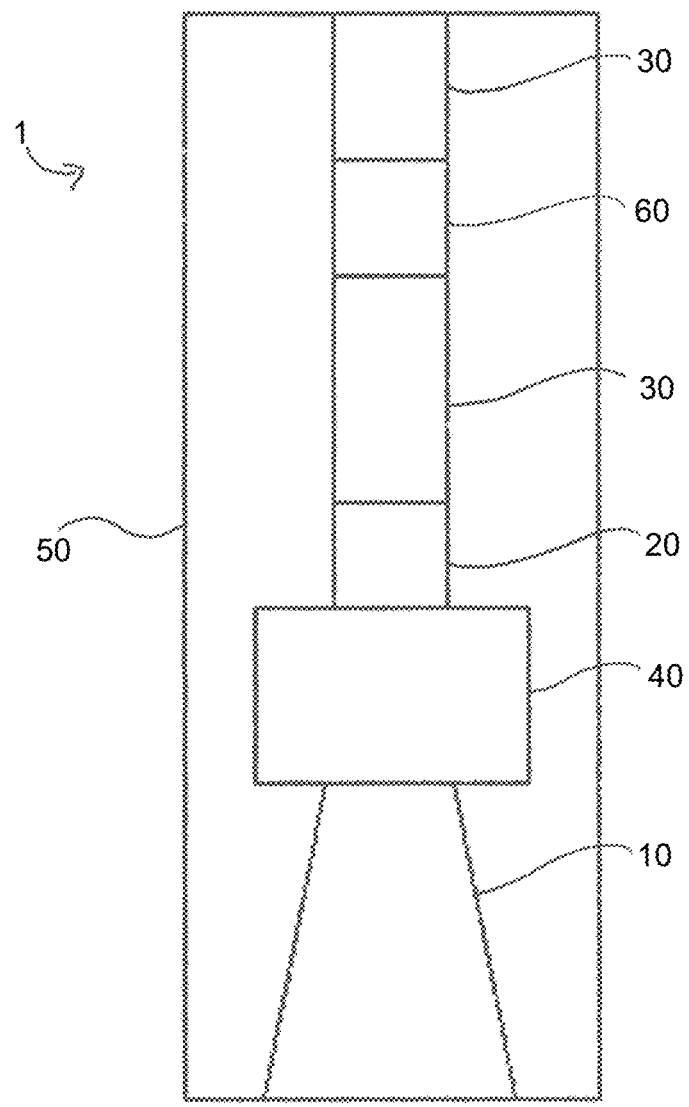
FIG. 6 is a schematic representation of a side view of the embodiment of FIG. 5.

Further, adjustment of the resonant properties of the housing 50 may be accomplished. This may even be accomplished during use of the device 1. For example, varying of internal dimension of the chambers 10, 30, 40 facilitates the altering in at least one embodiment of the frequency and/or frequencies at which the housing 50 resonates. Further, as shown in the preferred embodiment of FIGS. 5 and 6, a resonance adjustment member 60 is movably disposed at least partially within the primary resonance chamber 30. FIGS. 5 and 6 demonstrate two possible positions of the resonance adjustment member 60 within the primary resonance chamber 30, but should not be taken as being the only contemplated positions or otherwise construed as limiting. Accordingly, moving, such as by sliding, telescoping, and/or any other suitable method, of the resonance adjustment member 60 within the primary resonance chamber 30 facilitates the alteration of resonant properties of the housing 50, and accordingly may facilitate a change in the acoustic signals which the device receives or to which the device is most tuned.

The embodiment of FIG. 1 further comprises a secondary resonance chamber 40 disposed in a sound receiving relationship relative to the acoustic capture chamber 10. The secondary resonance chamber facilitates "tuning" of the device 1, which should be understood as the adjusting of the range of acoustic signals that the device 1 receives or to which it is most sensitive. This may be accomplished by, for example, varying the dimensions of the secondary resonance chamber 40. Further, a proximal end 40' of the secondary resonance chamber 40 is in communication with the distal end 10" of the acoustic capture chamber 10. Additionally, a distal end 40" of the secondary resonance chamber is in communication with the proximal end 30' of the primary resonance chamber 30.

In various embodiments of the device 1, the acoustic capture chamber 10 and the secondary resonance chamber 40 are in fluid communication. Accordingly, the distal end 10" of the acoustic capture chamber and the proximal end 40' of the secondary resonance chamber are correspondingly structured such that fluid, e.g. air, passes between the two chambers 10, 40. This may further facilitate communication of acoustic signals between the chambers 10, 40.

Figure 7:
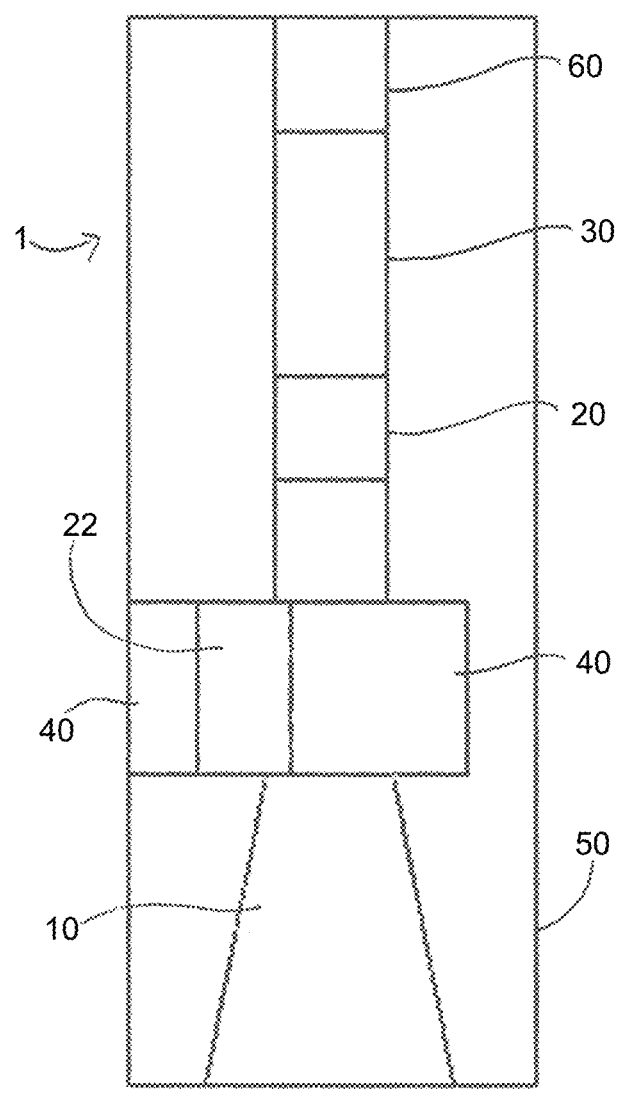
FIG. 7 is a schematic representation of a side view of an illustrative embodiment of a device in accordance with the present invention.

A preferred embodiment of a device 1, such as that of FIG. 1, further comprises at least one transducer 20 or, as shown in FIG. 7, a plurality of transducers 20, 22. An example of a transducer 20, 22 includes but is not limited to a microphone. The transducer 20, 22, such as shown in FIG. 1, is structured to convert the acoustic signal into at least one electrical signal. The electrical signal may then be processed, such as to facilitate diagnosis.

In addition, and with further reference to FIG. 1, the transducer 20 is disposed at least partially within the primary resonance chamber 30. However, the transducer 20 is not limited to disposition within the primary resonance chamber. Accordingly, it is contemplated that various other embodiments in accordance with the present invention comprise a transducer disposed at least partially in a corresponding one of the chambers 10, 30, 40.

Further, still other embodiments comprise a plurality of transducers, each of which is at least partially disposed in corresponding ones of the plurality of chambers 10, 30, 40. For example, and with reference to FIG. 7, at least one transducer, but preferably a plurality of transducers 20, 22 are disposed within the housing 50. Specifically, a first transducer 20 is preferably disposed at least partially within the primary resonance chamber 30, and a second transducer 22 is preferably disposed at least partially within the secondary resonance chamber 40. Further, the transducers 20, 22 may be movably disposed at least partially within their respective chamber. Accordingly, the transducers are independently and/or collectively moveable within their respective chamber or chambers. This facilitates alteration of the resonant properties of the housing 50 and/or alter frequencies of acoustic signals received by the transducers 20, 22 for conversion into at least one electrical signal.

Figure 3:
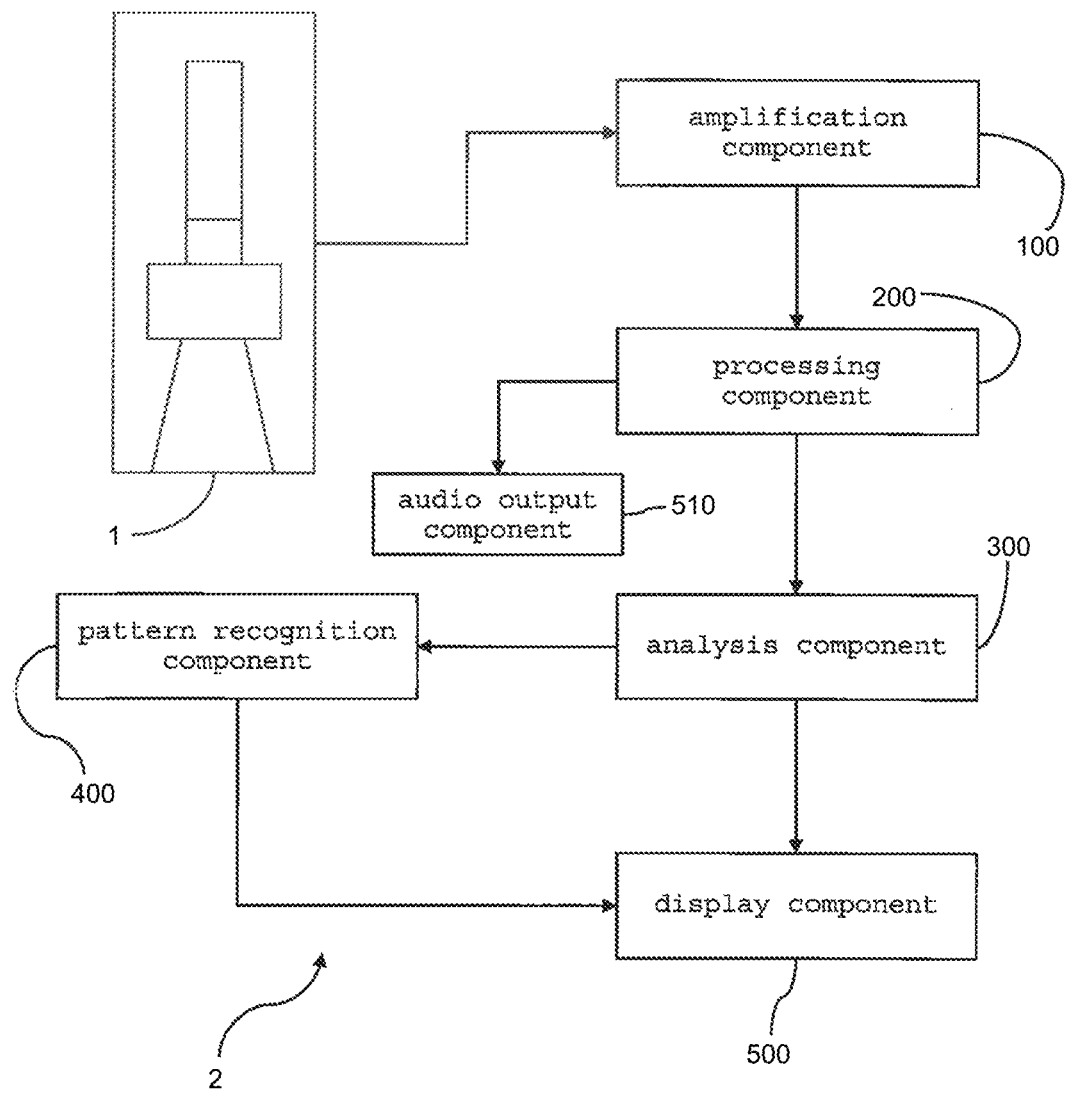
FIG. 3 is a schematic representation of an illustrative embodiment of a system in accordance with the present invention.

Turning now to FIG. 3, an embodiment of a system 2 in accordance with the present invention is provided. The system 2 comprises a device 1 for auscultation of a body. It should be appreciated that the device 1 may be the embodiment of FIG. 1, but may also be any embodiment of a device 1 consistent with the present invention. In a preferred embodiment of a system 2 as illustrated in FIG. 3, the device 1 is in communication with a plurality of components 100, 200, 300, 400, 500, 510. The components include, but are not limited to, a processing component 200, an analysis component 300, a pattern recognition component 400, and at least one output component 500, 510. The output components may comprise a display component 500 and an audio output component 510. Further, the system 2 may be configured to process the electronic signal using Dynamic Range Control and Equalization.

The amplification component 100 is structured to amplify an electronic signal received from the device 1. An example of an amplification component is a microphone preamplifier. The processing component 200 is structured to process the amplified signal received from the amplification component 200. The processing component 200 comprises a digital signal processor. Further, the processing component 200 is structured to process the amplified signal to facilitate further analysis. Additionally, the processing component 200 may be structured to incorporate pre-post AGC filtering, audio frequency dynamic range control and/or equalization. In a preferred embodiment, an audio output component 510 is in communication with the processing component 200. Accordingly, the audio output component 510 is structured to facilitate listening to the processed signal, such as by a medical professional. An example of an audio output component 510 includes headphones.

The analysis component 300 receives the processed signal from the processing component 200. The analysis component 300 is structured to produce an analyzed signal. Accordingly, the analysis component 300 may perform e.g. a Fast Fourier Transform analysis to produce the analyzed signal.

The analyzed signal is then transmitted to a pattern recognition component 400 structured to recognize patterns in the analyzed signal, such as those pertaining to any combination of the frequency, intensity or time domain. Further, the pattern recognition component 400 may be configured to match detected patterns in the analyzed signal with potential diagnosis and/or medical conditions. Accordingly, the pattern recognition component 400 is configured to output the potential diagnosis and/or medical condition in accordance with the corresponding detected pattern or patterns. The analyzed signal is further transmitted to a display component 500. Examples of a display component 500 include visual display devices structured for the output of a spectrogram. The display component 500 in various embodiments may further be configured to highlight issues detected by the system 2 and/or that may facilitate or otherwise aid in the diagnosis process.

Figure 8:
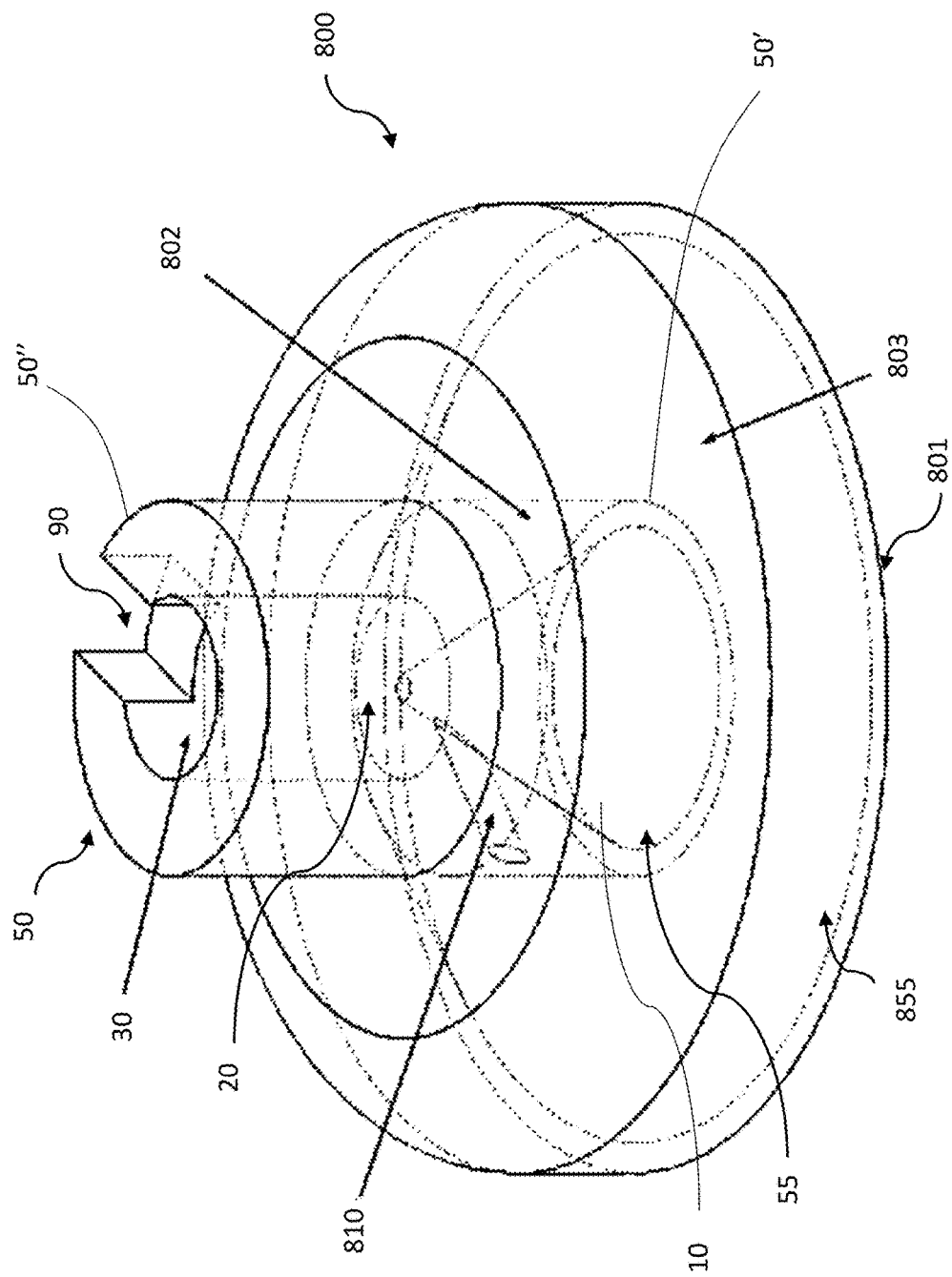
FIG. 8 is a schematic representation of another device in accordance with the present invention capable of receiving both higher and low frequencies sound signals.
Figure 9:
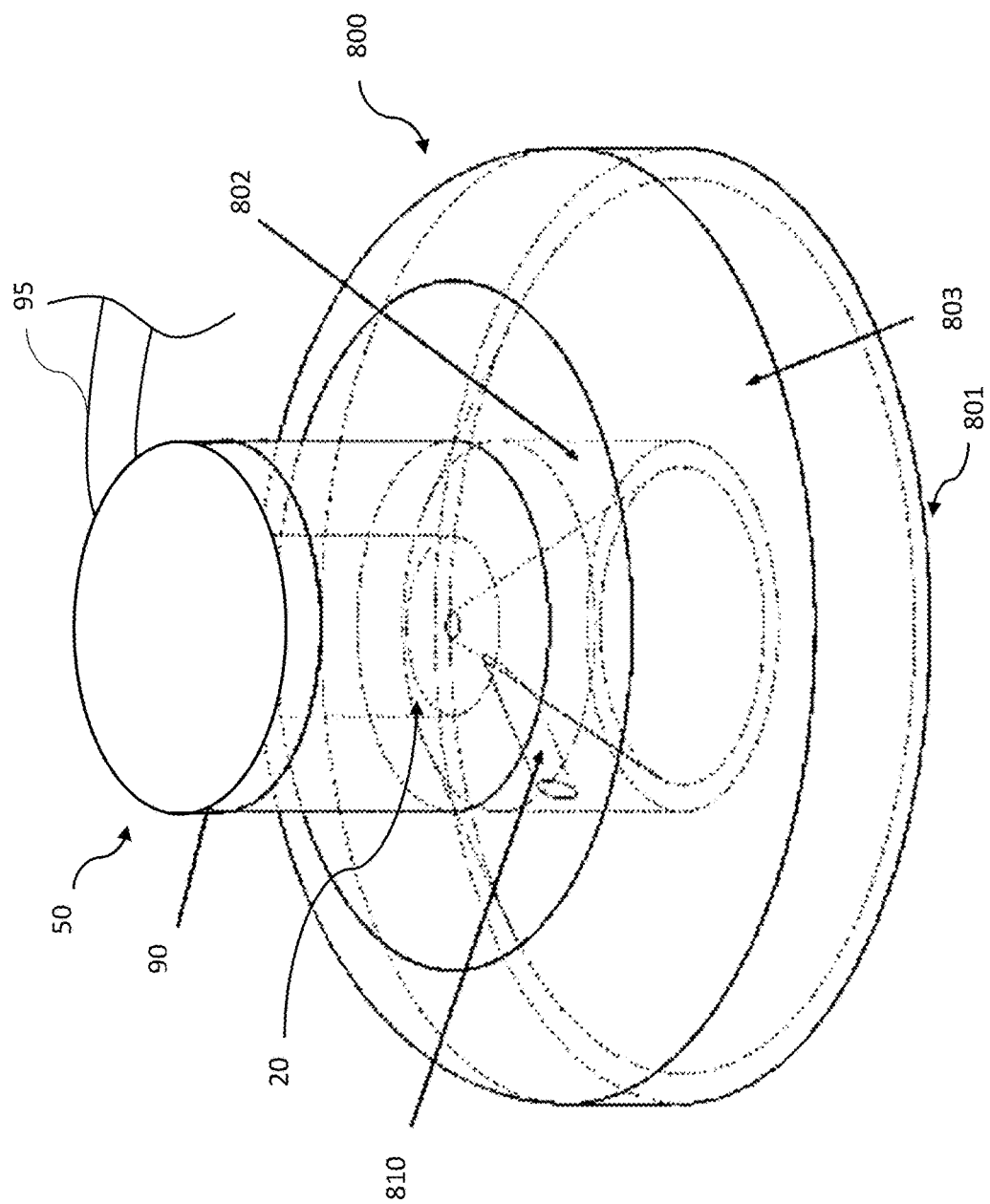
FIG. 9 is a schematic representation of an illustrative embodiment of a device in accordance with the present invention.
Figure 10:
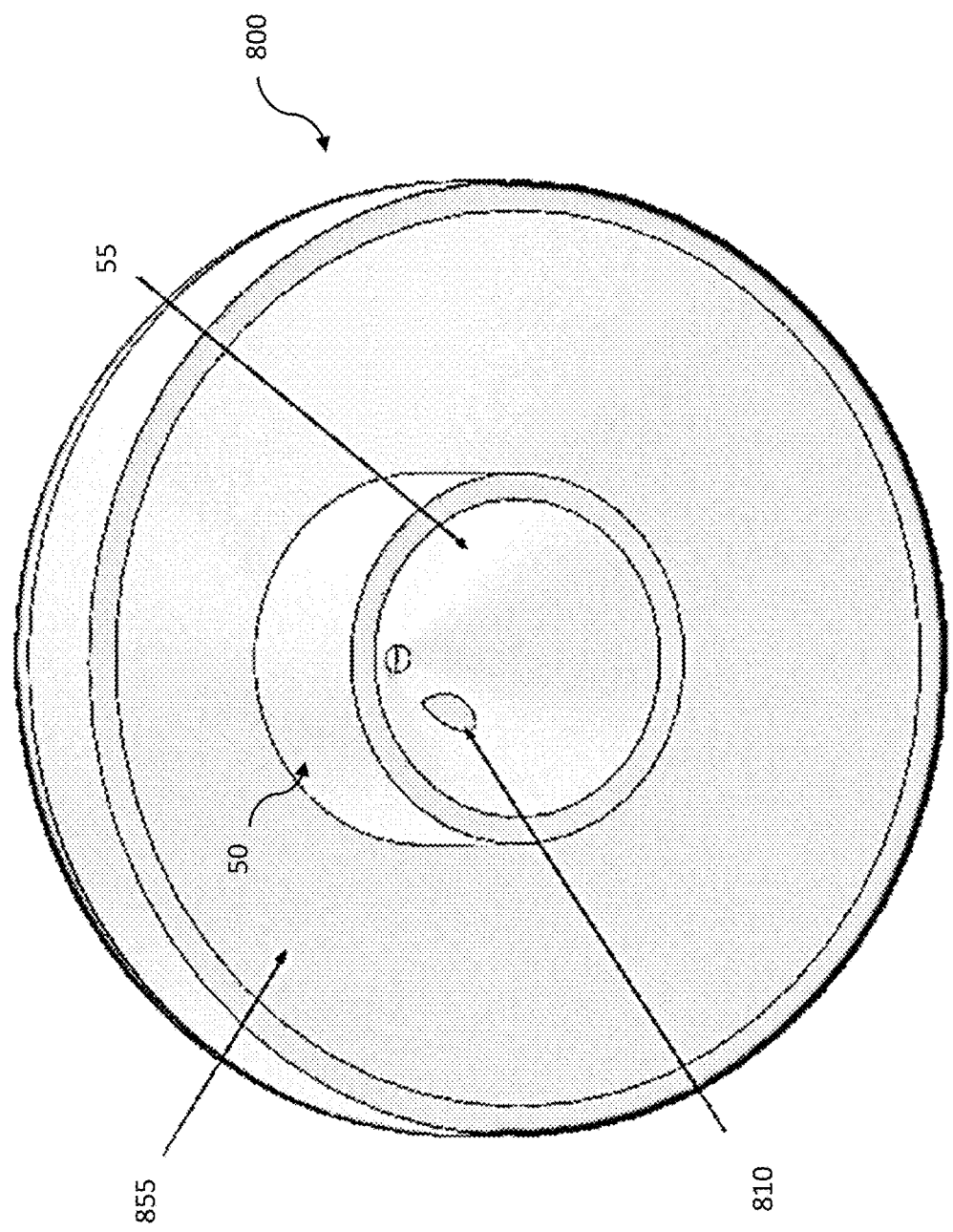
FIG. 10 is a schematic representation of a bottom view of the embodiment of FIG. 8.

While the above device embodiment is effective for frequencies above 500 Hz, in other additional embodiments it may also be desirable to capture lower frequency sounds, i.e. at or below 500 Hz. As such, the present invention further contemplates a device for auscultation of a body that may auscultate a wider range of frequencies, including those above and below 500 Hz simultaneously, as illustrated in FIGS. 8-10. Drawing attention to FIG. 8, a device 800 for auscultation of a body may comprise a housing 50 and concentric structure 800.

The housing 50 may comprise at least one of the embodiments for a device for auscultation as recited above, in accordance to FIGS. 1-7. As such, housing 50 may comprise a proximal end 50' and a distal end 50". The proximal end 50' of the housing 50 includes an opening 55 dimensioned and configured for engagement with a predetermined portion of a body when the housing 50 is disposed in an operative orientation relative to the body. The body may comprise a human or mammalian body which resonates internal sounds for auscultation, and the operative orientation may include placing the proximal end 50' of the housing in direct abutting relations to a portion of the body.

The housing 50 may further comprise a plurality of chambers disposed therewithin, which are collectively structured to receive an acoustic signal at least when the housing 50 is disposed in the operative orientation. At least one transducer 20 is at least partially disposed in a corresponding one of the chambers and structured to convert the received acoustic signal from the opening 55 of the housing 50 into an electrical signal.

The plurality of chambers may comprise an acoustic capture chamber 10 and a primary resonance chamber 30. A further secondary resonance chamber 40 may also be included, such as illustrated in the above embodiments of FIGS. 1-7. The transducer 20 is preferably disposed in the primary resonance chamber 30, which may also comprise a notch 90 for inserting a communications cable, such as 95, therethrough. However, the transducer 20 may also be disposed in another chamber, such as the secondary resonance chamber 40. Transducer 20 may comprise a microphone or any other combination of circuits or devices capable and appropriate for capturing converting acoustic sound waves into electrical input signals. The acoustic capture chamber 10 may comprise a conical profile, such that the distal end of the chamber comprises a diameter less than the diameter of the proximal end. The acoustic capture chamber 10 is disposed in a sound receiving relationship relative to the opening 55 of the housing 50. For instance, the opening 55 of the housing 50 may open into the acoustic capture chamber 55, as illustrated in FIG. 8. The shape, dimension, profile, and other configurations of the acoustic capture chamber is configured and intended to receive acoustic signals of at or above the 500 Hz frequency.

The concentric structure 800 is formed circumferentially in surrounding relations to the proximal end 50' of the housing 50, for capturing low frequency signals, such as those at or below 500 Hz. The concentric structure 800 may comprise a proximal end 801 and a distal end 802, the proximal end 801 includes the opening 855 dimensioned and configured for engagement with a predetermined portion of the body. The opening 855 of the concentric structure 800 is structured to receive the lower frequency signals of a resonating body. In at least one embodiment, the proximal end 801 of the concentric structure 800 may be parallel to the proximal end 50' of the housing 50. The distal end 802 of the concentric structure 800 may be formed circumferentially in abutting relations to an exterior of the housing 50. An exterior 803 of the concentric structure 801 may form a partial semi-dome, bell shape, or convex shape, while the distal portion 802 may be form a substantially flat profile.

In order to receive the low frequency signals from the concentric structure 800 at the transducer 20, the housing 50 comprises a low frequency receiver 810 in sound communication relations between the acoustic capture chamber 55 and the concentric structure 800. In the embodiment shown, the low frequency receiver 810 may comprise a bore 810, in accordance to FIGS. 8 and 10, formed from an interior opening of the concentric structure 800 to an interior of the acoustic capture chamber 55 in order to receive acoustic waves from the opening 855 of the concentric structure 800. In some embodiments, the low frequency receiver 810 may be structured to feed the signal directly into the primary resonance chamber 30 and/or the secondary resonance chamber 40 housing the transducer 20. The transducer 20 receives both the higher frequency signals from the opening 55 of the acoustic capture chamber 10, as well as the low frequency signals from the opening 855 of the concentric structure 800, through the low frequency receiver 810.

Both the higher frequency signals and the low frequency signals may then be either simultaneously or selectively converted into electrical input signals by the transducer, which may then be further processed for signal clarity or for desired audio effects as described above. The signal may travel up a communications cable 95 shown in FIG. 9 for this processing and/or may travel to another transducer such as an ear piece or headset which converts the electrical signals or processed electrical signals back into sound for a listener. In other embodiments, the cable 95 may be omitted and the transmission may occur wirelessly through methods known to those skilled in the art, such as but not limited to NFC, WiFi, Bluetooth, or other communication protocols. Also in accordance with an embodiment of FIG. 9, the transducer and the chamber it resides within, such as the primary resonance chamber 30, may be sealed with a cap 90, such as to prevent extraneous noise or interference.

Further embodiments of the present invention are directed to reducing ambient noise leakage into the auscultation device 1 and/or 800, as described above, through the use of one or more materials disposed therein and/or formed thereof.

In certain circumstances or environments, the auscultation device(s) of the present invention may be sensitive to extraneous acoustic or other vibrational interference, which may obscure important bio-acoustic data. The sensitivity of these extraneous interferences may predominantly be caused by two factors: (1) the material used to form the body of the auscultation device(s) do not sufficiently impede the transmission of unwanted vibrational energy into the inner chamber(s) thereof and/or to the acoustic capture device or microphone; and (2) the material used to form the outer body of the device resonates when excited by extraneous vibrational energy, and this is thereafter transmitted to the inner chamber(s) and/or acoustic capture device. The more sensitive the acoustic capture capabilities and broader the frequency response of the auscultation device, the greater is the susceptibility to any ambient noise leakage. As such, there is a need to further enhance the auscultation device 1 or 800 of the present invention, in order to overcome this further deficiency in the art.

Figure 11:
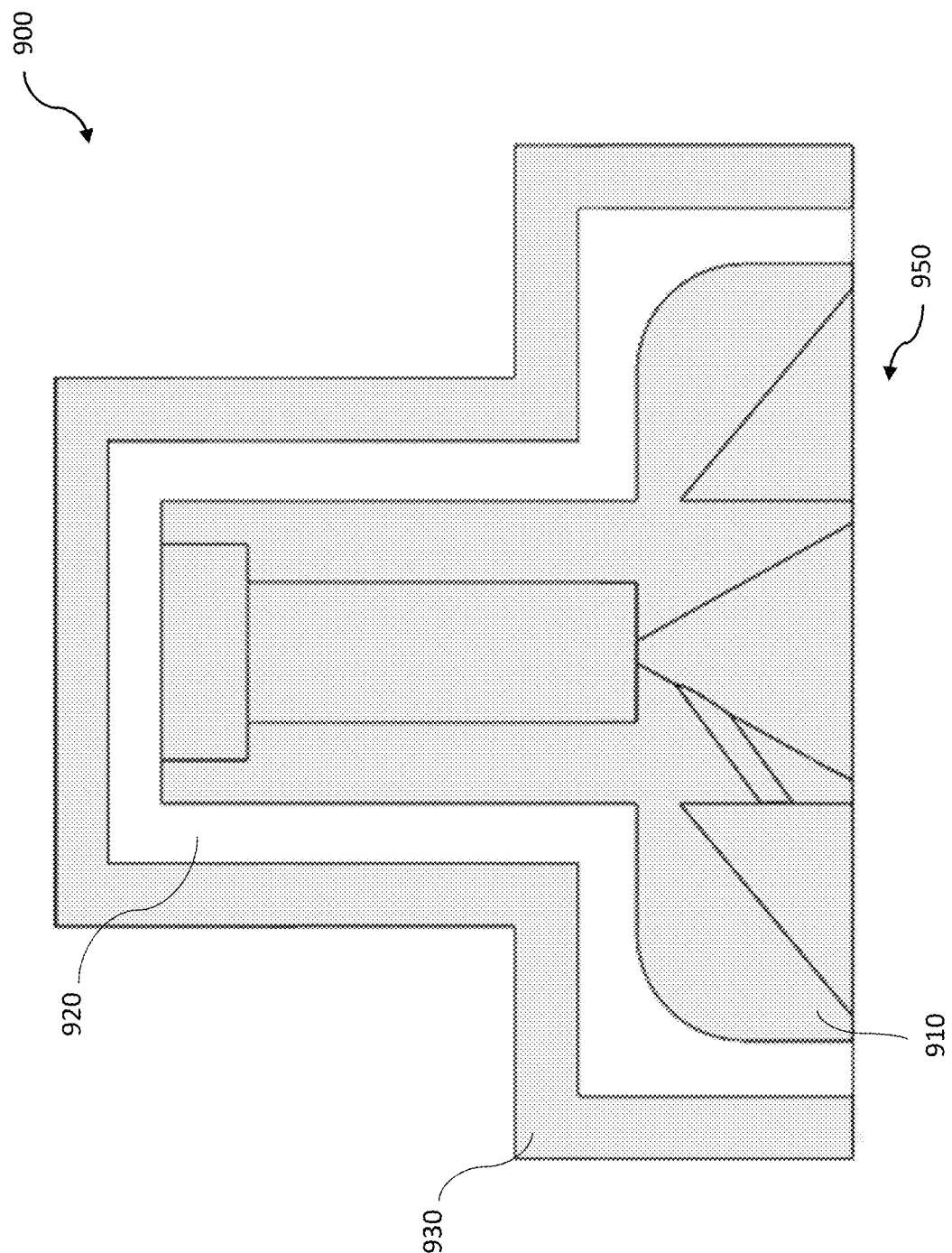
FIG. 11 is a schematic representation of a side cutaway view of a noise reduction assembly of the present invention.
Figure 12:
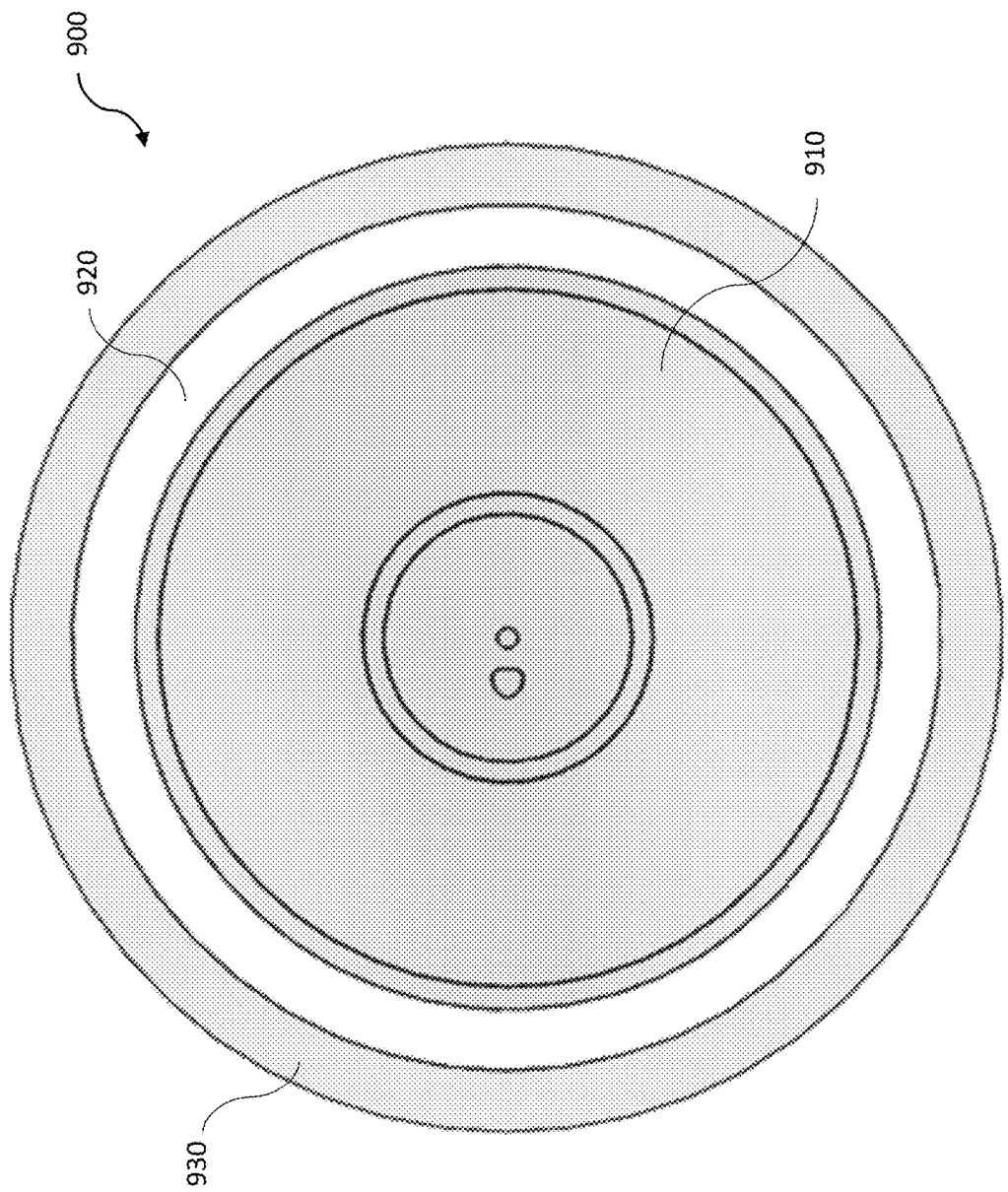
FIG. 12 is a schematic representation of a bottom view of a noise reduction assembly of the present invention.

In accordance with one embodiment of the present invention, and drawing attention to FIGS. 11 and 12, a noise reduction assembly 900 is represented in view of the structure of auscultation device 800 or another device for auscultation of a human or animal body.

Accordingly, an auscultation device 910, such as the device 800, or another device, may be provided as part of the overall assembly 900, which is formed of a first material. The first material may comprise aluminum, steel, stainless steel, high density plastic, HDPE, LDPE, polycarbonate, acrylic, ABS, PVC, Teflon, polypropylene, various woods, other metals, plastics, or other materials having sufficient rigidity appropriate for a handheld auscultation device. The interior structure of the auscultation device 910 may incorporate any one of the embodiments as described herein, such as that of the device 800 recited above.

An interior dampening layer 920 may be shrouded, as a layer on the outer body of all faces of the auscultation device 910 except its proximal end 950. In other words, the interior dampening layer 920 may be molded and disposed in abutting relations relative to an exterior surface of the auscultation device 910, and cover all exterior surfaces thereof except the proximal end as indicated by 950, which is the end placed upon a body for auscultation, or when the auscultation device is disposed in an operative orientation. The interior dampening layer 920 may be formed of a second material, which may comprise a putty, gel, foam, rubber formula, and/or any other preferably pliable material or combinations thereof.

An exterior dampening layer 930 may then be molded and disposed in abutting and covering relations relative to the interior dampening layer. In other words, it will form exterior to the interior dampening layer, and cover all of the interior dampening layer, as well as the auscultation device 910 therein, including all exterior surfaces of the auscultation device 910 except its proximal end as indicated by 950. The exterior dampening layer 930 may be formed of a third material, which may comprise aluminum, steel, stainless steel, high density plastic, HDPE, LDPE, polycarbonate, acrylic, ABS, PVC, Teflon, polypropylene, various woods, other metals, plastics, or other materials having sufficient rigidity to protect the interior dampening layer 920 and the auscultation device 910. In at least one embodiment, it is preferred that the third material will comprise a different and/or dissimilar material having a different material density, than the first material.

In other embodiments not shown, additional layering of multiple, dissimilar materials may be implemented in between the exterior dampening layer 930 and the interior dampening layer 920, in order to increase and/or enhance the impedance barrier and/or vibrational dampening characteristics of the overall assembly 900. Ideally and in one embodiment, each layer, including the auscultation device 910, the interior dampening layer 920, the exterior dampening layer 930, and any additional layers implemented and disposed in between the exterior 930 and interior 920 layers, are of dissimilar materials relative to its adjacent layer(s), in order to increase the performance or dampening effect of the overall assembly 900. For example, in one embodiment, the first material forming the auscultation device 910 may comprise stainless steel, the third material forming the exterior dampening layer 930 may comprise a plastic, and the second material forming the interior dampening layer 920 may comprise a gel.

That is, layering different materials having different densities and/or other characteristics may impede a greater frequency of noises or vibrations. For example, when the outermost (third) material is excited by an outside source, some frequencies will be stopped, some attenuated to various degrees and some will pass through virtually unchanged. The material itself will also want to resonate to some degree. The second material will act upon the first to damp or decrease any resonance. The vibrational energy that makes it through the outermost material will then be affected by the middle (second) material. This material will act as the previous except at different frequencies. In other words, entirely different frequencies will be stopped, attenuated or allowed to pass. Since this second material is pliable, it creates a significantly more effective impedance barrier than simply placing two rigid materials against each other. Much like transmitting vibrations from a solid wall into a pool of water. Any remaining vibrational energy will now reach the innermost (first) material. This material will act in the same fashion as the outermost and will be similarly affected by the middle material.

The system of layering or cascading different materials or dampening layers works to create multiple impedance barriers which significantly reduces the amount of vibrational energy that is transmitted through the device. It also damps the resonant characteristics of the, necessarily, rigid materials.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A noise reduction assembly for auscultation of a body comprising:
    an auscultation device comprising:
        a housing having an opening dimensioned and configured for engagement with a predetermined portion of the body when said housing is disposed in an operative orientation,
        said housing including a plurality of chambers disposed therewithin collectively structured to receive an acoustic signal at least when said housing is disposed in the operative orientation,
        at least one transducer at least partially disposed in a corresponding one of said chambers and structured to convert the acoustic signal into an electrical signal,
        a concentric structure formed circumferentially in surrounding relations to an end of said housing;
        a low frequency receiver disposed at least in sound communicating relation between said housing and said concentric structure, and structured to receive low frequency signals;
    a first dampening layer molded and disposed in abutting relation relative to an exterior surface of said housing and covering substantially all exterior surfaces thereof except at said end of said housing, and
    a second dampening layer molded and disposed in abutting and covering relation relative to said first dampening layer.

2. The assembly as recited in claim 1 wherein said plurality of chambers comprises an acoustic capture chamber disposed in a sound receiving relationship relative to said opening of said housing.

3. The assembly as recited in claim 2 wherein said housing comprises said low frequency receiver in sound communication relations between said acoustic capture chamber and said concentric structure.

4. The assembly as recited in claim 3 wherein said low frequency receiver comprises a bore formed from an interior opening of said concentric structure to an interior of said acoustic capture chamber in order to receive acoustic waves from the opening of said concentric structure.

5. The assembly as recited in claim 3 wherein said concentric structure comprises a proximal end and a distal end, said proximal end of said concentric structure including an opening dimensioned and configured for engagement with the predetermined portion of the body.

6. The assembly as recited in claim 2 wherein said proximal end of said concentric structure is parallel to said end of said housing.

7. The assembly as recited in claim 2 wherein said distal end of said concentric structure is formed circumferentially in abutting relation to an exterior of said housing.

8. The assembly as recited in claim 2 wherein said acoustic capture chamber comprises a distal end having a diameter less than a diameter of a proximal end of said acoustic capture chamber.

9. The assembly as recited in claim 2 wherein said plurality of chambers further comprises a primary resonance chamber disposed in a sound receiving relationship relative to said acoustic capture chamber.

10. The assembly as recited in claim 9 wherein said at least one transducer is disposed at least partially within said primary resonance chamber.

11. The assembly as recited in claim 9 wherein said primary resonance chamber comprises a sealed distal end.

12. The assembly as recited in claim 1 wherein said housing is formed of a first material selected from aluminum, steel, stainless steel, and high density plastic.

13. The assembly as recited in claim 12 wherein said first dampening layer is formed of a second material selected from a putty, gel, rubber, and foam.

14. The assembly as recited in claim 13 wherein said second dampening layer is formed of a third material selected from aluminum, steel, stainless steel, and high density plastic.

15. The assembly as recited in claim 14 wherein said first material and said third material are each formed of a different material having a different density.

* * * * *